United States Patent [19]

Haehn

[11] Patent Number: 4,701,190
[45] Date of Patent: Oct. 20, 1987

[54] PROCESS FOR RECOVERING METHYLACETYLENE AND/OR PROPADIENE

[75] Inventor: Peter C. Haehn, Geretsried, Fed. Rep. of Germany

[73] Assignee: Linde Aktiengesellschaft, Wiesbaden, Fed. Rep. of Germany

[21] Appl. No.: 927,978

[22] Filed: Nov. 7, 1986

[30] Foreign Application Priority Data

Nov. 7, 1985 [DE] Fed. Rep. of Germany ....... 3539553

[51] Int. Cl.4 ............................................. B01D 53/14
[52] U.S. Cl. ............................................ 55/49; 55/65; 55/84
[58] Field of Search ............................ 55/48, 49, 63-65, 55/83, 89; 585/534, 809, 864-867

[56] References Cited

U.S. PATENT DOCUMENTS

| | | | |
|---|---|---|---|
| 2,753,012 | 7/1956 | Thodos et al. | 55/65 X |
| 2,830,677 | 4/1958 | Coberly | 55/65 X |
| 2,993,566 | 7/1961 | Griffin | 55/65 X |
| 3,034,272 | 5/1962 | Griffin et al. | 585/867 X |
| 3,234,712 | 2/1966 | Lovett et al. | 55/65 X |
| 3,272,885 | 9/1966 | Davison | 55/65 X |
| 3,325,972 | 6/1967 | Friz et al. | 55/65 |
| 3,376,693 | 4/1968 | Rinaldi et al. | 55/65 |
| 3,390,535 | 7/1968 | Marshall | 585/867 X |
| 3,471,584 | 10/1969 | Platz et al. | 585/809 X |
| 3,635,038 | 1/1972 | Nagel et al. | 585/867 X |
| 3,657,375 | 4/1972 | Brunner et al. | 585/809 X |
| 3,686,344 | 8/1972 | Brunner et al. | 55/64 X |
| 4,106,917 | 8/1978 | Fields et al. | 55/64 X |
| 4,367,363 | 1/1983 | Katz et al. | 585/534 X |
| 4,540,422 | 9/1985 | Hampton | 585/867 X |
| 4,655,798 | 4/1987 | Ruch et al. | 55/64 |

FOREIGN PATENT DOCUMENTS 1020676 2/1966 United Kingdom ................... 55/65

OTHER PUBLICATIONS

Howard et al., *Petroleum Refiner*, DMF-Acetylene Recovery Solvent, Jan., 1954, pp. 143-146, vol. 33, No. 1.

Primary Examiner—Robert Spitzer
Attorney, Agent, or Firm—Millen & White

[57] ABSTRACT

For recovering methylacetylene and/or propadiene from a $C_3$-containing feed stream. The feed stream is treated with a first stream of physical solvent, e.g. DMF, under an elevated pressure to absorb the $C_3$-acetylenes. Propadiene is then selectively stripped from the loaded, first solvent stream and rescrubbed with a second solvent stream under a lower pressure. A residual gaseous stream may then be stripped from the second solvent, which gas may be further rescrubbed with a third stream of solvent to obtain an additional propadiene. Methylacetylene in the first solvent, as well as propadiene in the second or third solvent stream may then be recovered separately or together.

16 Claims, 1 Drawing Figure

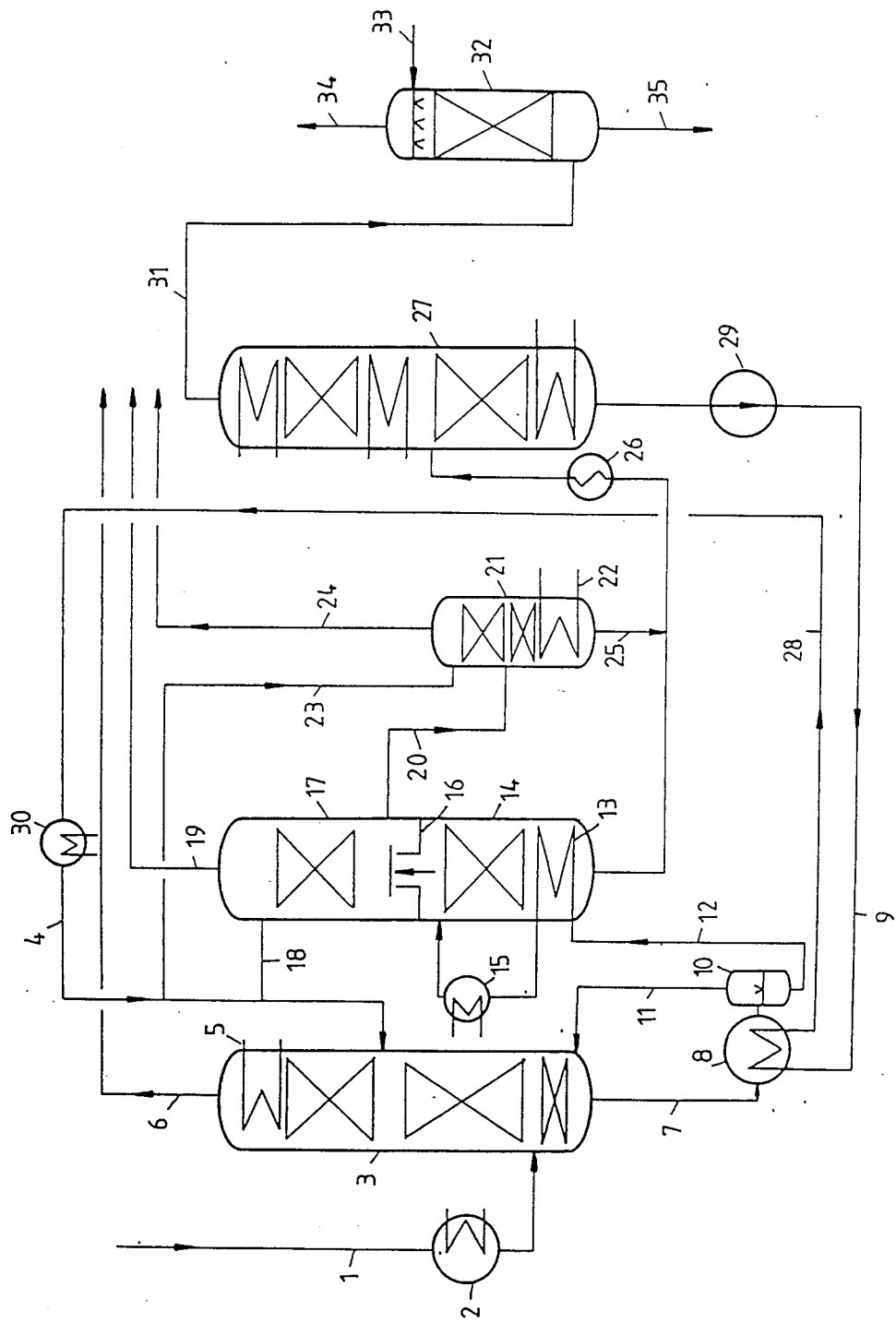

PROCESS FOR RECOVERING METHYLACETYLENE AND/OR PROPADIENE

Background of the Invention

The invention relates to a gas absorption process for the recovery of methylacetylene and/or propadiene from a $C_3$-containing feed stream by scrubbing with a physical solvent.

The cracked gases produced when cracking hydrocarbons for olefin manufacture contain methylacetylene and propadiene in small amounts. The cracked gases, after separation of heavy oil and cracked gasoline proportions, are conventionally compressed and then fractionated by rectification. During this process, a crude $C_3$-fraction is obtained consisting essentially (up to about 75-95 mol-%) of propylene and containing, in addition, a few percent of $C_3$-acetylenes, namely methylacetylene and propadiene, as well as propane.

According to German patent 2,149,184, it is possible to separate methylacetylene and propadiene from such a feed stream by scrubbing with dimethylformamide. The objective of this conventional process is to obtain, on the one hand, the $C_3$-acetylenes and, on the other hand, a propane/propylene mixture free of $C_3$-acetylenes. For this purpose, the feed stream is scrubbed countercurrently with dimethylformamide as the solvent, the solvent absorbing the $C_3$-acetylenes as well as a part of the propane and propylene. The loaded solvent, after expansion, is passed to a stripper-absorber operated in such a way that the solvent withdrawn from the sump is loaded with the same molar proportions of $C_3$-acetylenes and propylene/propane. Thus, a gaseous mixture consisting essentially of propane/propylene and small amounts of $C_3$-acetylenes can be withdrawn overhead.

In a subsequent regenerating column, the loaded solvent is freed entirely of the entrained gases, the latter being withdrawn in a desired ratio of 50 mol-% $C_3$-acetylenes and 50 mol-% or less of propane/propylene. It is also possible by means of this conventional process, to obtain from the head of the regenerating column a pure or enriched $C_3$-acetylene fraction and from the head of the stripper-absorber a propane/propylene fraction that is free of $C_3$-acetylene.

One disadvantage of the known process, however, is that the overhead product from the stripper-absorber constitutes a considerable proportion of the total gas quantity and must be reused for reasons of economy. Accordingly, this recycle gas must be compressed. Likewise, since energy must be expended for the compression of the stripping gas for the stripper-absorber, a great amount of energy must also be utilized in view of the very large quantities of scrubbing medium circulated. Moreover, the conventional process does not provide for the recovery of propadiene and methylacetylene separately from each other.

Summary of the Invention

An object of the present invention is to provide an improved energy-efficient process of the type discussed hereinabove.

Another object is to provide a process enabling separate recovery of propadiene and methylacetylene.

Upon further study of the specification and appended claims, further objects and advantages of this invention will become apparent to those skilled in the art.

To attain these objects, a process is provided comprising scrubbing methylacetylene and propadiene from a feedstream with a first solvent stream under elevated pressure; separating propadiene from resultant loaded, first solvent stream; and rescrubbing the separated propadiene with a second solvent stream under a lower pressure.

In a more comprehensive embodiment, propadiene is separated from the second solvent loaded essentially with propadiene, and methylacetylene is separated from the first solvent stream loaded essentially with methylacetylene.

The feed stream in the process of this invention generally comprises a $C_3$ stream containing significant quantities of propane, propylene and $C_3$-acetylenes. A particular $C_3$ stream is the bottoms product of a propane/propylene splitter containing usually about 20-40 mol-% $C_3$-acetylenes, about 20-50 mol-% propane, the remainder being propylene. This feed stream in a gas absorption step is scrubbed with an organic, physical solvent, such as, for example, dimethylformamide (DMF) or N-methylpyrrolidone (NMP) in a main absorption column under elevated pressure ranging generally between 2 and 20 bar, preferably between 6 and 12 bar, to obtain a purified gaseous mixture consisting essentially of propane and propylene ($<0.5$, preferably $<0.2\%$ by mols of methylacetylene + propadiene) as the overhead fraction from the absorber.

The solvent absorbs the $C_3$-acetylenes, and albeit to a more limited degree, propane and propylene. In order to liberate these gases, the loaded solvent is heated so that propane and propylene, owing to their lower solubility in the solvent, are desorbed into the gaseous phase. Heating of the solvent can advantageously take place in indirect heat exchange with completely regenerated solvent recovered hot from a thermal regeneration column, or by means of external heat. The thus-heated, propane/propylene-containing propane/propylene-containing gaseous phase can be removed in a phase separator and recycled to the aforesaid gas absorption step as stripping gas in order to increase the concentration of $C_3$-acetylenes in the loaded solvent, i.e. to drive out propane and propylene. By this feature, the amount of residual gas fractions from downstream stripper-absorber columns, as described below, can be maintained at low levels under low pressure, as compared to the absorber overhead product, for example, only 3-6% of the entire propane/propylene proportion in the feed gas.

In view of the fact that propadiene and methylacetylene exhibit different solubilities in physical solvents, e.g. DMF or NMP, it is possible to release propadiene selectively from the loaded, first solvent. This is preferably conducted in a stripping column downstream of the main absorption column. During this step, preferably employing indirect heat exchange, methylacetylene is concentrated in the bottom of the stripping column, and propadiene is driven off overhead. Stripping of the loaded, first solvent in the bottom of the stripping column can proceed to such an extent that only highly pure methylacetylene is left in the solvent. This purified methylacetylene can then be separated from the solvent in a further column, e.g. by thermal regeneration. If there is no necessity for obtaining high-purity methylacetylene, then it is advantageous to leave about 60-90, preferably 80 mol-% the methylacetylene and about, 30-60 preferably 50 mol-% of the propadiene in the solvent, based on the amount in the original feed.

The gas leaving the stripping column, greatly enriched with propadiene, is selectively rescrubbed, according to this invention, with a second solvent stream under a lower pressure of advantageously 1-3 bar, but in any case lower in pressure than the pressure in the main absorber, preferably by at least, especially by at least bar. The second solvent stream is advantageously a partial stream, preferably 30-50 mol-%, of the first solvent. The quantity of resultant rescrubbed residual $C_3$-fraction can be kept very small, as indicated above, due to the preliminary stripping that has taken place, and can be discharged without additional compression, for example as heating gas. The second solvent stream, loaded essentially with propadiene, is treated in a downstream stripper/absorber to separate the entrained gases, propane and propylene, the latter gases being referred to as "inert" gases in the context of their low solubility in the solvent. A third solvent stream can be used to recover any propadiene entrained in the inert residual gas. This second residual $C_3$-fraction can also be kept very small in its amount on account of the preliminary stripping step performed, and can also be discharged without additional compression, for example as heating gas.

At least two solvent streams are thus present in the process according to this invention, one being loaded essentially with propadiene and the other essentially with methylacetylene. These two solvent streams can be freed separately of propadiene and methylacetylene respectively.

For this purpose the heat exchanger 26 and the columns 27 and 32 have to be provided twice and operated in parallel. The individually regenerated solvent fractions are combined and pumped back via pump 29.

A preferred way of conducting such separation is merely by boiling off the desired gases from the solvent, using steam as an indirect heat transfer agent.

Separation of propadiene and/or methylacetylene takes place preferably under a pressure of between 1 and 3 bar. This also holds true for the separation of propadiene from the loaded, first solvent.

The separate recovery, i.e. desorption/absorption of propadiene and methylacetylene is possible on account of the differing solubilities of the two $C_3$-acetylene isomers in the physical solvent, especially DMF or NMP.

In case it is desired to obtain a pure propadiene fraction and a head product consisting essentially of methylacetylene and propadiene, instead of a pure methylacetylene fraction, then it is possible, according to one embodiment of the process of this invention, to admix the second stream of solvent, freed of propadiene, to the first solvent loaded with methylacetylene and to feed it to a $C_3$-acetylenes separation together with this first solvent. This mode of operation offers the advantage that propadiene separation from the first solvent need not be complete. Rather, a certain residual amount of propadiene and thus also entrained methylacetylene can remain in the second solvent inasmuch as also these residual amounts are obtained as the overhead product in the regeneration step. If, in this connection, a very high purity of the $C_3$-acetylene products is demanded, then it is advantageous to scrub the overhead gaseous product from the final regenerating column with water in order to remove entrained solvent from the thus-obtained gaseous fraction.

According to another, especially preferred embodiment of the process according to this invention, separation and scrubbing of propadiene can be performed in a single column which is subdivided into an upper section and a lower section by means of a chimney tray or a similar device.

Consequently, the process of this invention makes it possible to produce, if desired, on the one hand, a pure propadiene fraction and, on the other hand, either a pure methylacetylene fraction or a mixture of methylacetylene and propadiene. Low operating costs are also possible, since substantially only low-pressure steam and cooling water and, in small amounts medium-pressure steam are required. Very small quantities of coolant are also utilized, merely for the reduction of solvent losses.

BRIEF DESCRIPTION OF THE DRAWING

For purposes of facilitating an understanding of the invention the attached figure is a schematic flowsheet of a comprehensive, preferred embodiment of the invention.

DETAILED DESCRIPTION OF THE DRAWING

By way of conduit 1, a feed stream in the amount of 4,684 kg/h is introduced. The feed stream, a bottom product from a $C_3$-splitter has the following composition:

31 mol-% methylacetylene +propadiene
24 mol-% propane
45 mol-% propylene.

The feed stream is obtained in the liquid phase and thus is first of all vaporized in a vaporizer 2. The feed stream is then conducted at a temperature of 24° C. into the lower part of an absorber 3 and scrubbed countercurrently to regenerated solvent (23,700 kg/h of DMF at a temperature of 32° C.) introduced via conduit 4. A pressure of 9 bar is ambient in the absorption column 3 during this step. The $C_3$ overhead product practically free of acetylenes, cooled slightly to 18° C. with the aid of a coolant 5 in order to condense out DMF vapors, is discharged by way of conduit 6 in a quantity of 3,093 kg/h. Less than 0.5 mol-% of $C_3$-acetylenes is contained in this overhead product.

The loaded DMF is stripped in the bottom of absorber 3 with hot (about 150° C.) propane/propylene vapors to concentrate the $C_3$-acetylenes in the DMF phase and to drive out propane/propylene.

The propane/propylene vapors are produced in the following way. The loaded DMF is discharged from the absorber via conduit 7 at a temperature of 82° C. In a heat exchanger 8, the loaded solvent is heated to about 150° C. by indirect heat exchange with completely regenerated solvent (37,400 kg/h) introduced via conduit 9. During this heating step, the concomitantly dissolved inert gases propane and propylene are released and can be withdrawn from a separator 10 via conduit 11 and utilized as the stripping gas, which has the typical composition: $C_3$-acetylenes 60 mol %, propane/propylene 20% and DMF 20 mol %.

Loaded DMF (25,274 kg/h) discharged via conduit 12 from the separator 10 transfers its heat in a reboiler 13 ployed in a downstream stripping (stripper-absorber) column 14, thus being cooled to 114°C. After further cooling against cooling water in a cooler 15° to 54°C., the loaded DMF is introduced into the upper section of the stripper 14, operated under 2 bar, and stripped with the vapor generated in the reboiler, thus separating 577 kg/h of a gaseous fraction which contains, besides propadiene, also propane, propylene, and methylacetylene.

This gaseous fraction rises upwardly at a temperature of 54° C. and passes via a chimney tray 16 into an absorber section 17 located in the same column. In this section, the gaseous fraction is scrubbed under a pressure of 1.8 bar with a second solvent stream, specifically 8,200 kg/h of DMF branched off via conduit 18 from the regenerated solvent of conduit 4. By way of conduit 19, 64 kg/h of propane/propylene is removed from the absorber section at a temperature of 35° C.

The second solvent stream (8,700 kg/h), loaded essentially with propadiene, is withdrawn from the lower section of the absorber at a temperature of 46° C. via conduit 20 and fed into a stripper/absorber column 21 operated at 1.8 bar. In column 21, the inert gas proportions propane and propylene are driven out of the DMF by means of vapor generated in a reboiler 22. In order to increase the propadiene yield, a third solvent stream, specifically 5,500 kg/h of regenerated DMF is introduced via conduit 23 into the upper section of column 21. Via conduit 24, 37 kg/h of the residual inert gas propane/propylene, and trace quantities of propadiene and/or methylacetylene, is discharged from the stripper at a temperature of 36° C.

By way of conduit 25, 14.2 t/h of solvent (78° C.), loaded essentially with methylacetylene and/or propadiene is discharged from the sump of column 21 and, together with 24.7 t/h of first solvent (86° C.), loaded with methylacetylene and/or propadiene, from stripper 14, is heated in a heat exchanger 26 against low-pressure steam to 109° C. and introduced into a regenerating column 27. In the latter, the DMF is stripped with vapor generated in the reboiler by medium-pressure steam. The pure DMF, at a temperature of 169° C., can be withdrawn via conduit 9 provided with pump 29 by means of which the DMF, after being cooled in heat exchanger 8 to 93° C., and cooled in a cooler 30 to 32° C., is reintroduced by way of conduits 28 and 4 into the absorbers 3, 17 and the stripper/absorber column 21.

At the head of the column 27, 551 kg/h of propadiene, 790 kg/h of methylacetylene, as well as 8 kg/h of solvent vapors are withdrawn at −8° C. via conduit 31 from the regenerating column 27. For obtaining a high-purity $C_3$-acetylenes product, this overhead fraction from the regenerating column 27 is introduced into a scrubber 32 charged with scrubbing water via conduit 33. Accordingly, DMF-free $C_3$-acetylene can be recovered via conduit 34. Water loaded with DMF is discharged by way of conduit 35.

| Operating Requirements | |
| --- | --- |
| Low-pressure steam | 1.8 t/h |
| Medium-pressure steam | 3 t/h |

Cooling water requirement based on a 10° C. temperature increase: 200 t/h, or with the use of air coolers, the cooling water demand can be typically reduced to 100 t/h.

By low pressure and medium pressure steam is meant steam supplied at a minimum of approximately 1,5 kg/cm$^2$ and 16 kg/cm$^2$ respectively.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A gas absorption process for the recovery of methylacetylene and/or propadiene from a $C_3$-containing feed stream comprising scrubbing the feed stream in an absorber column with a first stream of solvent under an elevated pressure to absorb methylacetylene and propadiene; selectively stripping propadiene from resultant loaded first stream solvent to provide a gaseous phase containing mostly propadiene and a minor amount of residual gas fraction; rescrubbing stripped propadiene with a second solvent under a lower pressure to absorb propadiene selectively from the residual gas fraction; and separating propadiene from resultant second solvent loaded selectively with propadiene, and separating methylacetylene from resultant first stream of solvent loaded selectively with methylacetylene.

2. A process according to claim 1, wherein the separation of propadiene and/or methylacetylene is performed by stripping.

3. A process according to claim 1, wherein the absorption with the first stream solvent is conducted under a pressure of 2-20 bar, and with the second stream of solvent under a lower pressure of between 1 and 3 bar.

4. A process according to claim 3, wherein the absorption with the first solvent is conducted under a pressure of 6-12 bar.

5. A process according to claim 1, wherein propadiene and/or methylacetylene is separated from the solvent under a pressure of 1-3 bar.

6. A process according to claim 1, wherein the second solvent stream selectively loaded with propadiene, is introduced into the first solvent stream selectively loaded with methylacetylene.

7. A process according to claim 6, further comprising scrubbing resultant separated propadiene and/or methylacetylene with water in order to remove entrained solvent therefrom.

8. A process according to claim 1 wherein the second solvent stream is a partial stream of the first solvent stream.

9. A process according to claim 8, wherein the partial stream utilized as the second solvent constitutes about 30-50% of the first solvent.

10. A process according to claim 1 further comprising heating the loaded, first solvent prior to propadiene separation to obtain a gas predominating in propane and/or propylene.

11. A process according to claim 10, wherein the heating of the loaded, first solvent is conducted by indirect heat exchange with completely regenerated solvent.

12. A process according to claim 11, further comprising passing resultant gas obtained after heating the loaded, first solvent, as stripping gas, countercurrently to the loaded, first solvent in the bottom part of the absorber column.

13. A process according to claim 10, further comprising passing resultant gas obtained after heating the loaded, first solvent, as stripping gas, countercurrently to the loaded, first solvent in the bottom part of the absorber column.

14. A process according to claim 1 wherein the separation and rescrubbing of propadiene is conducted in a single column.

15. A process according to claim 1 wherein the methylacetylene and propadiene are stripped off separately from each other from the respected solvent streams loaded with methylacetylene and propadiene, and are recovered as separate products.

16. A gas absorption process for the recovery of methylacetylene and/or propadiene from a $C_3$-containing feed stream comprising scrubbing the feed stream in an absorber column with a first stream of solvent under an elevated pressure to absorb methylacetylene and propadiene; and selectively stripping propadiene from resultant loaded first stream solvent to provide a gaseous phase containing mostly propadiene and a minor amount of residual gas fraction.

* * * * *